(12) United States Patent
Beattie

(10) Patent No.: US 6,376,235 B1
(45) Date of Patent: Apr. 23, 2002

(54) **IVI-2, IVI-3 AND IVI-4 LOCI OF *ENTEROCOCCUS FAECALIS* POLYNUCLEOTIDE, POLYPEPTIDES AND METHOD OF USE THEREFOR**

(75) Inventor: David Beattie, Roslindale, MA (US)

(73) Assignee: Avant Immunotherapeutics, Inc., Needham, MA (US)

( * ) Notice: Subject to any disclaimer, the term of this patent is extended or adjusted under 35 U.S.C. 154(b) by 0 days.

(21) Appl. No.: 09/147,857

(22) PCT Filed: Sep. 18, 1997

(86) PCT No.: PCT/US97/16589

§ 371 Date: Mar. 16, 1999

§ 102(e) Date: Mar. 16, 1999

(87) PCT Pub. No.: WO98/12205

PCT Pub. Date: Mar. 26, 1998

Related U.S. Application Data

(60) Provisional application No. 60/025,899, filed on Sep. 18, 1996.

(51) Int. Cl.[7] .............................................. C12N 15/00
(52) U.S. Cl. ................. 435/320.1; 435/70.1; 435/71.1; 536/23.1; 536/23.7
(58) Field of Search ............................. 435/70.1, 71.1, 435/69.1, 320.1; 530/300, 350; 536/23.1, 23.7

(56) References Cited

PUBLICATIONS

The Primer, random pd(N)6 kit (Boehringer Mannheim Biochemicals 1991 Catalog), 1991.*

Herzog et al., DNA and Cell Biology, 12(6):465–474, 1993.*

Rudinger et al., in "Peptide Hormones", edited by Parsons, J.A., University Park Press, Jun. 1976, p. 6, 1976.*

Gold, et al., Database BIOSIS on Dialog, No.: 99494305, Gold, H.S. "Detection of Genes Involved in the Pathogenesis of Experimental Enterococcal Endocarditis Using in vivo Expression Technology (IVET)," abstract, Abstracts of the Interscience Conference on Antimicrobial Agents and Chemotheraphy, vol. 36, No. 0, 1996, p. 33.

* cited by examiner

*Primary Examiner*—Donna C. Wortman
*Assistant Examiner*—Robert A. Zeman
(74) *Attorney, Agent, or Firm*—Elliot M. Olstein; Alan J. Grant

(57) ABSTRACT

The present invention provides polynucleotides coding for the mature transcriptional regulators known as ivi-2 and ivi-3, as well as a polynucleotide coding for a polypeptide designated as ivi-4. The polynucleotides were obtained from a genomic library obtained from the bacterial species *Enterococcus faecalis*.

15 Claims, 4 Drawing Sheets

FIG. 1A

```
                                                          50
                                                           *
G ATC ATC TGT TGC  TAG TTC AAC AAT AAG CTT TAC GTT TGG CAT GAT TTC CAA AAT GAA
C TAG TAG ACA ACG  ATC AAG TTG TTA TTC GAA ATG CAA ACC GTA CTA AAG GTT TTA CTT
<---D  D   T   A   L   E   V   I   L   K   V   N   P   M   I   E   L   I   F

100
                                                           *
ATC AAT CAT CTT TTG TTT TTC TGG CAT ATT TTCACCT CCTATCCAAATGTAAAGAGTCATAACGAGTCATA
TAG TTA GTAGAA AAC AAAAAG ACC GTA TAAAAGTGGAGGATAGGTTTACATTCT CAGTATTGCTCAGTAT
 D   I   M   K   Q   E   P   M  <--ORF2          rbs 150
                                                           *
G TTA TTC AAA AAA AAG TGT CCA ATC AAA ACC CAA AAT TGA TTT TTA ACT ACG AGC GTA TCG TGA
C AAT AAG TTT TTT TTC ACA GGT TAG TTT TGG GTT TTA ACT ACG AGC GTA TCG TGA
  END E   F   F   F   L   T   W   D   F   G   L   I   S   A   I   R   M   A   S 200
                                                           *
TTC CAC AGA CGG TCT TCT TCT TCC CTG TTC AAT AGA TGC ATA TGT GGT TCT TGA AAT TTC
AAG GTG TCT GCC AGA AGA AGA AGG GAC AAG TTA TCT ACG TAT ACA CCA AGA ACT TTA AAG
 E   V   S   P   R   R   R   G   Q   E   I   S   A   Y   T   T   R   S   I   E

MATCH WITH FIG. 1B
```

FIG. 1B

MATCH WITH FIG. 1A

```
                 250                                    300
                  *                                      *
CGC TTT AAC GGC AAC CTC TTC TTG AGT CAT TTT ATT TTT TAT ACG CAA TTT CAA TAG CCA
GCG AAA TTG CCG TTG GAG AAG AAC TCA GTA AAA ATA TAA AAA ATA TGC GTT AAA GTT ATC GGT
 A   K   V   A   V   E   E   Q   T   M   K   N   K   I   R   L   K   L   W

350
                                                         *
ATC TCT CAT TTTACGTCC TCCTTTA TGTGTCGTATTGCGTACTTTTATAA TACTACGCATTTTGACACACGTCAAC
TAG AGA GTA AAATGCAGG AGGAAAT ACACAGCATAACGCATGAAAATATT ATGATGCGTAAAACTGTGTGCAGTTC
 D   R   M <- ORF1        rbs                                                 35
                          400
                           *
AATTAATTAC TCTTTTGACACATTCAATATA TTAACTTCAAACTACGCATATTGGTAGTATTATATGTACATAAGGA
TTAATTAATG AGAAAACTGTGTAAGTTATAT AATTGAAGTTTGATGCGTATAACGCATCATATATACATGTATTGCT
            -35                                                            450
                                                                             *
                                                     -10
                  500
                   *
ATCGTAGG AGGTAAC ATT ATG TTC GGT ACA CGC TTA ACA GAA TTA AGG AAA CAA AAA AAA TTA
TAGCATCC TCCATTG TAA TAC AAG CCA TGT GCG AAT TGT CTT AAT TCC TTT GTT TTT AAT
   rbs        ivi-2 ->  M   F   G   T   R   L   T   E   L   R   K   Q   K   K   L
```

MATCH WITH FIG. 1C

FIG. 1C

MATCH WITH FIG. 1B

```
                                           550
                                            *
ACA CAA ACT GAT GTT GCA AAT GCA CTT GGT GTA GCT AGA ACG ACT TAC TCT TCC TAT GAA
TGT GTT TGA CTA CAA CGT TTA CGT GAA CCA CAT CGA TCT TGC TGA ATG AGA AGG ATA CTT
 T   Q   T   D   V   A   N   A   L   G   V   A   R   T   T   Y   S   S   Y   E

600
                    *
CAA GGA AGA AGA ACT CCA GAT ATA GAT CTA TAG GTT TTA TTC TAA CGA CTG ATA AAG TTA CAT
GTT CCT TCT TCT TGA GGT CTA TAT CTA GAT ATC CAA AAT AAG ATT GCT GAC TAT TTC AAT GTA
 Q   G   R   R   T   P   D   I   D   L   *   V   L   F   *   R   L   I   K   L   H
                                  (Q   G   R   R   T   P   D   I   D   I   Q   N   K   I   A   D   Y   F   N   V)

650
        *                                                                       700
                                                                                 *
AGT CTA GAT TAT TTA CAT GGG AGA GAA AGT TTT GAA GAT ACT TCC TTA TCA AAA AAA CAA
TCA GAT CTA ATA AAT GTA CCC TCT CTT TCA AAA CTT CTA TGA AGG AAT AGT TTT TTT GTT
 S   L   D   Y   L   H   G   R   E   S   F   E   D   T   S   L   S   K   K   Q
```

MATCH WITH FIG. 1D

FIG. 1D

MATCH WITH FIG. 1C

```
                                                   750
         *                                          *
TTA ACC GTC GCT GCT CAT ATA GAC GAT GAC GTT TCA GAT ACA GAA ATG AAT GAG ATT CTC
AAT TGG CAG CGA CGA GTA TAT CTG CTG CAA AGT CTA TGT CTT TAC TTA CTC TAA GAG
 L   T   V   A   A   H   I   D   D   D   V   S   D   T   E   M   N   E   I   L

*
TCT TTT CAT TGA   TTAT ATT AAGAAA CGCG ATC
AGA AAA GTA ACT   AATATAATT CTTTGCGCTAG
 S   P   H  END
```

IVI-2, IVI-3 AND IVI-4 LOCI OF *ENTEROCOCCUS FAECALIS* POLYNUCLEOTIDE, POLYPEPTIDES AND METHOD OF USE THEREFOR

This Application is a national stage filed application based on PCT/US97/16589, filed Sep. 18, 1997.

This application claims priority of U.S. Provisional Application Ser. No. 60/025,899, filed Sep. 18, 1996, the disclosure of which is hereby incorporated by reference in its entirety.

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as transcriptional regulators.

Transcriptional regulators are factors that assist RNA polymerase to more accurately initiate and conduct transcription. Some transcription factors are general factors required for all promoters while others are gene-specific and are required only for certain promoters. Some general factors are also involved in the assembly of a multi-component protein complex of the promoter.

Transcriptional factors usually are found to have at least two functional domains, one for binding DNA and one for transcriptional activation. These functions are frequently found within circumscribed structural domains which frequently retain their function even when removed from the place of their natural occurrence.

Generally, *Enterococcus faecalis* is a pathogenic bacteria species which is known to cause infections, particularly endocarditis, in mammals. Therefore, suppression of a transcriptional regulator in such a bacteria would be detrimental to the growth of the bacteria and limit its ability to infect a host with endocarditis.

In accordance with one aspect of the present invention, there are provided novel transcriptional regulator polypeptides, as well as active fragments, analogs and derivatives thereof.

In accordance with another aspect of the present invention, there are provided isolated nucleic acid molecules encoding the transcriptional regulators of the present invention including mRNAs, cDNAs, genomic DNAs as well as active analogs and fragments of such transcriptional regulators.

In accordance with another aspect of the present invention there are provided isolated nucleic acid molecules encoding mature polypeptides expressed by the DNA contained in ATCC Deposit No. 98167.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said transcriptional regulators and subsequent recovery of said transcriptional regulators.

In accordance with yet a further aspect of the present invention, there is provided a process for utilizing such transcriptional regulators as reagents for testing pharmaceutical antibiotics for their activity in deactivating or controlling the activity of the transcriptional regulators as part of a screening process to identify pharmaceuticals for treating or controlling *Enterococcus faecalis* infections.

In accordance with another aspect of the present invention the polynucleotides or epitopic fragments thereof are useful as in vitro agents for producing monoclonal antibodies useful in screening procedures for diagnosing *Enterococcus faecalis* bacterial infections by identifying the presence of such bacteria in a specimen from a mammal suspected of having such an infection. Also, such polynucleotides or epitopic fragments are useful as reagents to test pharmaceutical chemicals for activity in suppressing the expression of such polynucleotides. Thus, the polynucleotides and polypeptides according to the invention are useful as in vitro agents for diagnostic and screening procedures for identifying and/or treating *Enterococcus faecalis* infections in mammals.

In another aspect of the present invention, an antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of the *E. faecalis* ivi locus genes. The antisense RNA oligonucleotide hybridizes to the mRNA in vivo and blocks translation of mRNA molecules into transcriptional regulator polypeptides (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the ivi locus transcriptional regulators.

In accordance with yet a further aspect of the present invention, there are also provided nucleic acid probes comprising nucleic acid molecules of sufficient length to specifically hybridize to a nucleic acid sequence of the present invention.

In accordance with yet a further aspect of the present invention, there is provided a process for utilizing such transcriptional regulator polypeptides, or polynucleotides encoding such polynucleotides, for in vitro purposes related to scientific research, for example, to generate probes for identifying similar sequences which might encode similar transcriptional regulators from other organisms by using certain regions, i.e., conserved sequence regions, of the nucleotide sequence.

These and other aspects of the present invention should be apparent to those skilled in the art from the teachings herein.

BRIEF DESCRIPTION OF THE DRAWINGS

The following drawings are illustrative of an embodiment of the invention and are not meant to limit the scope of the invention as encompassed by the claims.

FIG. 1

FIG. 1, Panels 1A through 1D collectively, are a contiguous illustration of the full-length DNA sequence (SEQ ID NO:1) and the corresponding deduced amino acid sequences for the IVI-2 locus of *Enterobacteria faecalis* which is a transcriptional regulator of the present invention, as well as two other open reading frames and an intergenic region. Thus, Panel 1A has the beginnings of the sequences, and Panel 1B continues through Panel 1D with the last of the sequences.

DEFINITIONS

In order to facilitate understanding of the following description and examples which follow certain frequently occurring methods and/or terms will be described.

The term "gene" means the segment of DNA involved in producing a polypeptide chain; it includes regions preceding and following the coding region (leader and trailer) as well as intervening sequences (introns) between individual coding segments (exons).

A coding sequence is "operably linked to"another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A DNA "coding sequence of" or a "nucleotide sequence encoding" a particular enzyme, is a DNA sequence which is transcribed and translated into a polypeptide when placed under the control of appropriate regulatory sequences.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel et al., *Nucleic Acids Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in Sambrook and Maniatis, Molecular Cloning: A Laboratory Manual, Cold Spring Harbor Laboratory, 1989.

In accordance with an aspect of the present invention, there are provided isolated nucleic acids (polynucleotides) which encode for the mature ivi-2 polypeptide, for a second mature ivi-3 polypeptide, and for a portion of a polypeptide ivi-4, having the deduced amino acid sequences shown collectively by FIG. 1 (SEQ ID NOS:2, 4 and 6, respectively).

In accordance with another aspect of the present invention, there are provided isolated polynucleotides encoding the ivi-2 and ivi-3 polypeptides, as well as the partial polypeptide of ivi4 of the present invention. The deposited material is a genomic clone comprising DNA encoding the ivi-2, ivi-3 and partial ivi-4 polypeptides of the present invention, in a plasmid DNA vector form designated as pEFivi2. As deposited with the American Type Culture Collection, 10801 University Blvd, Manassas, Va. 20110-2209 USA, the deposited material is assigned ATCC Deposit No. 98167, and was deposited on Sep. 12, 1996.

The deposit has been made under the terms of the Budapest Treaty on the International Recognition of the Deposit of Micro-organisms for Purposes of Patent Procedure. The clone will be irrevocably (without restriction or condition) released to the public upon the issuance of a patent. This deposit is provided merely as convenience to those of skill in the art and is not an admission that a deposit would be required under 35 U.S.C. §112. The sequence of the polynucleotide contained in the deposited material, as well as the amino acid sequence of the polypeptide encoded thereby, are controlling in the event of any conflict with any description of sequences herein. A license may be required to make, use or sell the deposited material, and no such license is hereby granted.

DETAILED DESCRIPTION OF THE INVENTION

Transcriptional regulators are a group of key polypeptides involved in phage lysogeny, sporulation, plasmid transfer, and amino acid utilization, as well as other activities. Such polypeptides are found in a number of bacterial species.

The polynucleotide of this invention coding for the ivi-2 and ivi-3 transcriptional regulators and the partial polypeptide of ivi-4 was originally recovered from a genomic gene library derived from *Enterococcus faecalis*, of the genus Enterococcus. The particular strain of bacteria was JH2-2.

The polynucleotides of this invention having transcriptional regulation activity was cloned and recovered from a genomic gene library from *Enterococcus faecalis* strain JH2-2. Clones were obtained and one such clone was called EFivi2 and the plasmid harbored by it was called pEFivi2. The plasmid DNA was isolated from XL1-Blue for DNA sequencing.

The sequence of the entire insert of pEFivi2 was obtained using an ABI Model 377 Automated Sequencer with dye-terminator and cycle sequencing chemistry. The completed sequence was analyzed using the MacVector sequence analysis program. The insert was found to be 798 base pairs in length (SEQ ID NO: 1) and to contain two complete and one partial open reading frames (ORFs). (See FIG. 1.) One coding for a 98 amino acid sequence polypeptide (SEQ ID NO:3) is designated as the ivi-2 gene (SEQ ID NO:2). A second ORF sequence coding for a 61 amino acid IVI-3 (SEQ ID NO:5) is transcribed in the opposite direction and is designated IVI-3 (SEQ ID NO:4). The partial ORF, of which 28 amino acids (SEQ ID NO:7) were identified, lies 45 bases downstream of ORF and is designated IVI-4 (SEQ ID NO:6). All three are preceded by putative ribosome binding sites (AGGAGG). The 164 base intergenic region between ivi-2 and ivi-3 appears to contain putative promoters capable of driving divergently transcribed genes. Further, ivi-2 is preceded by the elements TTCAA and TATTAT, and ivi-3 is preceded by TTGACG and TATTAT, which are similar to the −35 (TTGACA) and −10 (TATAAT) consensus sequences recognized by *Bacillus subtilis* σ containing RNA polymerase. As neither a terminator nor a promoter lie between the end of ORF#1 and the beginning of ORF#2, it is likely that both are encoded by the same transcript RNA.

Identity searches of non-redundant protein databases were performed for each ORF using the BLAST algorithm. The hypothetical protein encoded by ivi-2 shows identity to 17 database entries with p values less than 0.01. All are members of the PBSX family of transcriptional regulators, which tends to confirm the predicted activity of the protein. ORF#1 (ivi-3) shows identity to 13 database entries with p values less than 0.01. These are also members of the PBSX family, and many of the same gene products are hit by both ORFs. The top scoring match for ivi-3 and the second scoring match for ivi-2 are two genes organized in the same divergent arrangement with comparable intergenic space as ORF#1 and ivi-2. These are hypothetical proteins from the skin element locus of *B. subtilis*.

One means for isolating the nucleic acid molecules encoding the transcriptional regulator polypeptides of the present invention is to probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). For example, the partial gene sequence of ivi-4 is useful as a probe for obtaining the full length gene from a genomic library. It is appreciated by one skilled in the art that the polynucleotides of SEQ ID NOS:1, or fragments thereof (comprising at least 12 contiguous nucleotides), are particularly useful probes. Other particularly useful probes for this purpose are hybridizable fragments of the sequence of SEQ ID NO:1 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9. M NaCl, 50 mM $NaH_2PO_4$, pH 7.0, 5.0 mM $Na_2EDTA$, 0.5% SDS, 10× Denhardt's, and 0.5 mg/mL polyriboadenylic acid. Approximately $2 \times 10^7$ cpm (specific activity $4-9 \times 10^8$ cpm/ug) of $^{32}P$ end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1×SET at Tm less 10° C. for the oligo-nucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. Further, it is understood that a section of a 100 bps sequence that is 95 bps in length has 95% identity with the 190 bps sequence from which it is obtained. See J. Sambrook et al., *Molecular Cloning, A Laboratory Manual*, 2d Ed., Cold Spring Harbor Laboratory (1989) which is hereby incorporated by reference in its entirety. Also, it is understood that a fragment of a 100 bps sequence that is 95 bps in length has 95% identity with the 100 bps sequence from which it is obtained.

As used herein, a first DNA (RNA) sequence has a percent identity to another DNA (RNA) sequence if there is such percent identity between the bases of the first sequence and the bases of the another sequence, when properly aligned with each other, for example when aligned by BLASTN.

The present invention relates to polynucleotides which differ from the reference polynucleotide in a manner such that the change or changes is/are silent change(s), in that the amino acid sequence encoded by the polynucleotide remains the same. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

The polynucleotides of the present invention may be in the form of RNA or DNA which DNA includes cDNA, genomic DNA, and synthetic DNA. The DNA may be double-stranded or single-stranded, and if single stranded may be the coding strand or non-coding (anti-sense) strand. The coding sequences which encodes the mature transcriptional regulators according to the invention may be identical to the coding sequences shown in FIG. 1, collectively, (SEQ ID NO: 1) or may be a different coding sequence which coding sequence, as a result of the redundancy or degeneracy of the genetic code, encodes the same polypeptides and putative promoters as the DNA of FIG. 1, collectively, (SEQ ID NO: 1).

As hereinabove indicated, the polynucleotides may have a coding sequence which is a naturally occurring allelic variant of the coding sequence shown in FIGS. 1A–1B, collectively, (SEQ ID NO:1). As known in the art, an allelic variant is an alternate form of a polynucleotide sequence which may have a substitution, deletion or addition of one or more nucleotides, which does not substantially alter the function of the encoded polypeptide. Also, using directed and other evolution strategies, one may make very minor changes in DNA sequence which can result in major changes in function.

Fragments of the full length gene of the present invention may be used as hybridization probes for a cDNA or a genomic library to isolate the full length DNA and to isolate other DNAs which have a high sequence identity to the gene. Probes of this type preferably have at least 10, preferably at least 15, and even more preferably at least 30 bases and may contain, for example, at least 50 or more bases. In fact, probes of this type having at least up to 150 bases or greater may be utilized. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides, having a sequence complementary to that of the gene or portion of the gene sequences of the present invention are used to screen a library of genomic DNA to determine which members of the library the probe hybridizes to in a complementary sense, have an identity as described above.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95% identity between the sequences. (As indicated above, 70% identity would include within such definition a 70 bps fragment taken from a 100 bp polynucleotide, for example.) The present invention particularly relates to polynucleotides which hybridize under stringent conditions to the hereinabove-described polynucleotides. As herein used, the term. "stringent conditions" means hybridization will occur only if there is at least 95% and preferably at least 97% identity between the sequences. The polynucleotides which hybridize to the hereinabove described polynucleotides in a preferred embodiment encode transcriptional regulators which either retain substantially the same biological function or activity as the ivi-2 polypeptide encoded by the DNA of FIG. 1, collectively, (SEQ ID NO: 1). In referring to identity in the case of hybridization, as known in the art, such identity refers to complementarity of polynucleotide segments.

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotide of SEQ ID NO: 1, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the polypeptides of SEQ ID NOS:3, 5 and 7, respectively, as well as fragments thereof, which fragments have at least 15 bases, preferably at least 30 bases, more preferably at least 50 bases and most preferably fragments having up to at least 150 bases or greater, which fragments are at least 90% identical, preferably at least 95% identical and most preferably at least 97% identical to any portion of a polynucleotide of the present invention.

The present invention further relates to polypeptides which have the deduced amino acid sequence of FIG. 1, collectively, (SEQ ID NOS:3, 5 and 7, respectively) as well as fragments, analogs and derivatives of such polypeptide.

The terms "fragment", "derivative" and "analog" when referring to the polypeptides having the amino acid sequence of SEQ ID NOS:3, 5 and 7, respectively, means polypeptides which retain essentially the same biological function or activity as such polypeptides. Thus, an analog includes a proprotein which can be activated by cleavage of the proprotein portion to produce an active mature polypeptide.

The polypeptides of the present invention may be a recombinant polypeptide, a natural polypeptide or a synthetic polypeptide, preferably a recombinant polypeptide.

The fragment, derivative or analog of the polypeptides of SEQ ID NOS.3, 5 and 7, respectively, may be (i) one in which one or more of the amino acid residues are substituted with a con served or non-conserved amino acid residue (preferably conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptides of SEQ ID NOS:3, 5 and 7, respectively, (in particular the mature polypeptide) as well as polypeptides which have at least 70% similarity (preferably at least 70% identity) to the polypeptides of SEQ ID NOS:3, 5 and 7, respectively, and more preferably at least 90% similarity (more preferably at least 90% identity) to the polypeptides of SEQ ID NOS:3, 5 and 7, respectively, and still more preferably at least 95% similarity (still more preferably at least 95% identity) to the polypeptides of SEQ ID NOS:3, 5 and 7, respectively, and also include portions of such polypeptides with such portion of the polypeptide generally containing at least 30 amino acids and more preferably at least 50 amino acids and most preferably at least up to 150 amino acids.

As known in the art "similarity" between two polypeptides is determined by comparing the amino acid sequence and its conserved amino acid substitutes of one polypeptide to the sequence of a second polypeptide. The definition of 70% similarity would include a 70 amino acid sequence fragment of a 100 amino acid sequence, for example, or a 70 amino acid sequence obtained by sequentially or randomly deleting 30 amino acids from the 100 amino acid sequence.

A variant, i.e. a "fragment", "analog" or "derivative" polypeptide, and reference polypeptide may differ in amino acid sequence by one or more substitutions, additions, deletions, fusions and truncations, which may be present in any combination.

Among preferred variants of polypeptides according to the invention are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the transcriptional regulator polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector such as an expression vector. The vector may be, for example, in the form of a plasmid, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing the polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS, ptrc99a, pKK223-3, pDR540, pRIT2T (Pharmacia); Eukaryotic: pXT1, pSG5 (Stratagene) pSVK3, pBPV, pMSG, pSVL SV40 (Pharmacia). However, any other plasmid or vector may be used as long as they are replicable and viable in the host.

The genes described above and shown in FIG. 1 for ivi-2, ivi-3, and the partial for ivi-4 may be isolated from the deposited plasmid pEFivi-2 by the following digests:

ivi-2—418 basepair HincII-Sau3AI fragment ivi-3—2909 basepair HphI-HincII fragment ivi-4—102 basepair Sau3AI-MnII fragment.

All of the restriction enzymes for obtaining such fragments are commercially available through New England Biolabs.

For example, the ivi-2 gene product may be expressed by digesting plasmid pEFivi-2 with HincII and Sau3AI and the 418 basepair fragment containing the ivi-2 gene is then isolated from an agarose gel. The fragment is used in a ligation with plasmid pBluescript KS (Stratagene), which has been previously digested with HincII and BamHI. This places the ivi-2 gene and its native promoter downstream of the lac promoter contained on the vector. The ligation products are transformed into XL-1 Blue (Stratagene) and transformants are selected on LB agar containing 0.1 mg/ml ampicillin. Colonies are selected and screened for presence of the insert. Liquid cultures are grown in LB broth 0.1 mg/ml ampicillin to a density of 0.1 $A_{600}$ and IPTG is added at 1 mM to induce expression of the lac promoter and consequently the expression of the ivi-2 gene.

The same approach may be utilized for obtaining the ivi-3 gene product, except that T4 DNA polymerase blunt-ending of the fragment after gel purification and ligation with HincII digested pBluescript would be used for the expression of ivi-3.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology*, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition*, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM 1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

For preparation of monoclonal antibodies, any technique which provides antibodies produced by continuous cell line cultures can be used. Examples include the hybridoma technique (Kohler and Milstein, *Nature*, 256:495–497, 1975), the trioma technique, the human B-cell hybridoma technique (Kozbor et al., *Immunology Today* 4:72, 1983), and the EBV-hybridoma technique to produce human monoclonal antibodies (Cole et al., in *Monoclonal Antibodies and Cancer Therapy*, Alan R. Liss, Inc., pp. 77–96, 1985).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic polypeptide products of this invention.

Antibodies generated against a transcriptional promoter of the present invention may be used in screening for similar transcriptional promoters from other organisms and samples. Such screening techniques are known in the art, for example, one such screening assay is described in Sambrook and Maniatis, Molecular Cloning: A Laboratory Manual (2d Ed.), vol. 2:Section 8.49, Cold Spring Harbor Laboratory, 1989, which is hereby incorporated by reference in its entirety.

The present invention will be further described with reference to the following examples; however, it is to be understood that the present invention is not limited to such examples. All parts or amounts, unless otherwise specified, are by weight.

EXAMPLE 1

To help confirm the transcriptional activity of the ivi-2 gene, the gene was inactivated. An internal fragment of the gene corresponding to amino acids 18 through 86 was generated using PCR using the oligonucleotides GTC-GAGTCGACTGATGTTGCAAATGCACTT and GCAGGGTCGACGTCATCGTCTATATGAGCA, (SEQ ID NOS:8 and 9, respectively). These oligonucleotides added SalI sites to the ends for cloning into plasmid pBRΩKM-2. The PCR internal fragment and the plasmid were digested with SalI and ligated together to form a new plasmid. The resulting plasmid which was incapable of replication in *E. faecalis*. Electrotransformation of JH2-2 and integration of the plasmid onto the chromosome is by recombination at the cloned ivi-2 internal fragment, which disrupts and inactivates the gene. The electrotransformants of JH2-2 demonstrate very poor growth in kanamycin, despite carrying the Km-2 gene. When they are grown in the absence of the antibiotic, the cells appear to rapidly excise and segregate the plasmid. This data indicates that ivi-2 is an essential gene for growth.

EXAMPLE 2

In order to express the ivi-2 gene product, plasmid pEfivi-2 is digested with HincII and Sau3A1 and the 418 basepair fragment containing the ivi-2 gene is isolated from an agarose gel. It is used in a ligation with plasmid pBluescript KS (Stratagene), which has been previously digested with HincII and BamHI. This places the ivi-2 gene and its native promoter downstream of the lac promoter contained on the vector. The ligation products are transformed into XL-1 Blue (Stratagene) and transformants are selected on LB agar containing 0.1 mg/ml ampicillin. Colonies are selected and screened for presence of the insert. Liquid cultures are grown in LB broth 0.1 mg/ml ampicillin to a density of 0.1 $A_{600}$ and IPTG is added to 1mM to induce expression of the lac promoter and expression of the ivi-2 gene. Expression of the 11.2 kD gene product is monitored on an SDS-polyacrylamide gel.

EXAMPLE 3

In order to express the ORF1 (ivi-3) gene product, plasmid pEfivi-2 is digested with HincII and HphI and the 299 basepair fragment containing the ivi-3 gene is isolated from and agarose gel. It is treated with T4 DNA polymerase to make the HphI end blunt. It is then used in a ligation with plasmid pBluescript KS (Stratagene), which has been previously digested with HincII. This places the ivi-2 gene and its native promoter downstream of the lac promoter contained on the vector. The ligation products are transformed into XL1 Blue (Stratagene) and transformants are selected on LB agar containing 0.1 mg/ml ampicillin. Colonies are selected and screened for presence of the insert. Liquid cultures are grown in LB broth 0.1 mg/ml ampicillin to a density of 0.1 $A_{600}$ and IPTG is added at 1 mM to induce expression of the lac promoter and expression of the ivi-2 gene. Expression of the 7.2 kD gene product is monitored on an SDS-polyacrylamide gel.

EXAMPLE 4

In order to express and purify the ivi-2 gene product, plasmid pEfivi-2 is used as the template for PCR using the oligonucleotides CATATGTTCGGTACACGCTTA and CATATGTCAATGAAAAGAGAG (SEQ ID NOS:10 and 11, respectively). The 306 basepair PCR product containing the ivi-2 gene is digested with NdeI and isolated from an agarose gel. It is used in a ligation with plasmid pET-15b (Novagen), which has been previously digested with NdeI. This places the ivi-2 coding sequences downstream of the lac and T7 promoters contained on the vector and adds sequences encoding a hexahistidine tag to the 5' end of the ivi-2 gene, creating a chimeric polypeptide product. The ligation products are transformed into BL21 (Novagen) and transformants are selected on LB agar containing 0.1 mg/ml ampicillin. Colonies are selected and screened for presence of the insert. Liquid cultures are grown in LB broth 0.1 mg/ml ampicillin to a density of 0.1 $A_{600}$ and IPTG is added at 1 mM to induce expression of the lac promoter and expression of the ivi-2 gene. Expression of the 11.2 kD gene product is monitored on an SDS-polyacrylamide gel. Cells are lysed and the lysate is passed through a histidine binding resin column (Novagen), which binds the chimeric protein. The protein is cluted with imidazole and the histidine tag is cleaved by addition of thrombim. This produces substantially purified ivi-2 polypeptide.

EXAMPLE 5

In order to express and purify the ivi-3 gene product, plasmid pEfivi-2 is used as the template for PCR using the oligonucleotides CATATGGAGGATTGGCTATTG and CATATGTTATTCAAAAAAAAG (SEQ ID NOS:12 and 13, respectively). The 196 basepair PCR product containing the ivi-3 gene is digested with HdeI and isolated from and agarose gel. It is used in a ligation with plasmid pET-15b (Novagen), which has been previously digested with NdeI. This places the ivi-3 coding sequences downstream of the lac and T7 promoters contained on the vector and adds sequences encoding a hexahistidine tag to the 5' end of the ivi-3 gene, creating a chimeric polypeptide product. The ligation products are transformed into B1.21 (Novagen) and transformants are selected on LB agar containing 01.mg/ml ampicillin. Colonies are selected and screened for presence of the insert. Liquid cultures are grown in LB broth 0.1 mg/ml ampicillin to a density of 0.1 $A_{600}$ and IPTG is added at 1 mM to induce expression of the lac promoter and expression of the ivi-3 gene. Expression of the 7.2 kD gene product is monitored on an SDS-polyacrylamide gel. Cells are lysed and the lysate is passed through a histidine binding resin column (Novagen), which binds the chimeric protein. The protein is eluted with imidazole and the histidine tag is cleaved by addition of thrombim. This produces substantially purified ivi-3 polypeptide.

Numerous modifications and variations of the present invention are possible in light of the above teachings and, therefore, within the scope of the appended claims, the invention may be practiced otherwise than as particularly described.

What is claimed is:

1. An isolated polynucleotide comprising a member selected from the group consisting of:
   (a) a polynucleotide encoding a polypeptide comprising amino acid 2 to 98 of SEQ ID NO: 3; and
   (b) the complement of (a).

2. The isolated polynucleotide of claim 1 wherein said member is (a).

3. The isolated polynucleotide of claim 1 wherein said member is (a) and said polypeptide comprises amino acids 1 to 98 of SEQ ID NO: 3.

4. The isolated polynucleotide of claim 1, wherein the polynucleotide is DNA.

5. The isolated polynucleotide of claim 1, wherein said polynucleotide is RNA.

6. A method of making a recombinant vector comprising inserting the isolated polynucleotide of claim 1 into a vector, wherein said polynucleotide is DNA.

7. A recombinant vector comprising the polynucleotide of claim 1, wherein said polynucleotide is DNA.

8. A recombinant host cell comprising the polynucleotide of claim 1, wherein said polynucleotide is DNA.

9. A method for producing a polypeptide comprising expressing from the recombinant cell of claim 8 the polypeptide encoded by said polynucleotide.

10. The isolated polynucleotide of claim 1, comprising a polynucleotide sequence which is at least 95% identical to nucleotides 1 to 798 of SEQ ID NO: 1.

11. The isolated polynucleotide of claim 10 comprising the polynucleotide of SEQ ID NO: 1.

12. An isolated polynucleotide comprising a member selected from the group consisting of:
    (a) the 418 base pair polynucleotide formed after treatment of plasmid pEfivi-2 with the restriction nucleases HincII and Sau3A1, and
    (b) the complement of (a).

13. The isolated polynucleotide of claim 12, wherein the member is (a).

14. The isolated polynucleotide of claim 12, wherein the member is (b).

15. The isolated polynucleotide of plasmid pEfivi-2 contained in ATCC Deposit No. 98167.

* * * * *

SEQUENCE LISTING

```
<160> NUMBER OF SEQ ID NOS:  13

<210> SEQ ID NO 1
<211> LENGTH: 798
<212> TYPE: DNA
<213> ORGANISM: Enterococcus faecalis

<400> SEQUENCE: 1
gatcatctgt tgctagttca acaataagct ttacgtttgg catgatttcc aaaatgaaat      60
```

-continued

```
caatcatctt ttgtttttct ggcatatttt caccctcctat ccaaatgtaa agagtcataa      120
cgagtcatag ttattcaaaa aaaagtgtcc aatcaaaacc caaaattgat gcgattcgca      180
tagcactttc cacagacggt cttcttcttc cctgttcaat agatgcatat gtggttcttg      240
aaatttccgc tttaacggca acctcttctt gagtcatttt atttttttata cgcaatttca    300 atagccaatc tctcatttta cgtcctcctt tatgtgtcgt attgcgtact tttataatac     360
tacgcatttt gacacacgtc aacaattaat tactctttttt gacacattca atatatttaa   420
cttcaaacta cgcatattgc gtagtattat atgtacataa cgaatcgtag gaggtaacat    480
tatgttcggt acacgcttaa cagaattaag gaaacaaaaa aaattaacac aaactgatgt    540
tgcaaatgca cttggtgtag ctagaacgac ttactcttcc tatgaacaag gaagaagaac    600
tccagatata gatatccaaa ataagattgc tgactatttc aatgtaagtc tagattattt   660
acatgggaga gaaagttttg aagatacttc cttatcaaaa aaacaattaa ccgtcgctgc    720
tcatatagac gatgacgttt cagatacaga atgaatgag attctctctt ttcattgatt    780
atattaagaa acgcgatc                                                   798
```

```
<210> SEQ ID NO 2
<211> LENGTH: 297
<212> TYPE: DNA
<213> ORGANISM: Artificial Sequence
<220> FEATURE:
<223> OTHER INFORMATION: Description of Artificial Sequence:
      Polynucleotide encoding  IVI-2 polypeptide

<400> SEQUENCE: 2
```

```
atgttcggta cacgcttaac agaattaagg aaacaaaaaa aattaacaca aactgatgtt     60
gcaaatgcac ttggtgtagc tagaacgact tactcttcct atgaacaagg aagaagaact   120
ccagatatag atatccaaaa taagattgct gactatttca atgtaagtct agattattta    180
catgggagag aaagttttga agatacttcc ttatcaaaaa aacaattaac cgtcgctgct    240
catatagacg atgacgtttc agatacagaa atgaatgaga ttctctcttt tcattga       297
```

```
<210> SEQ ID NO 3
<211> LENGTH: 98
<212> TYPE: PRT
<213> ORGANISM: Artificial Sequence
<220> FEATURE:
<223> OTHER INFORMATION: Description of Artificial Sequence:Deduced
      amino acid sequence for  IVI-2 polypeptide

<400> SEQUENCE: 3
```

```
Met Phe Gly Thr Arg Leu Thr Glu Leu Arg Lys Gln Lys Lys Leu Thr
 1               5                  10                  15

Gln Thr Asp Val Ala Asn Ala Leu Gly Val Ala Arg Thr Thr Tyr Ser
                20                  25                  30

Ser Tyr Glu Gln Gly Arg Arg Thr Pro Asp Ile Asp Ile Gln Asn Lys
            35                  40                  45

Ile Ala Asp Tyr Phe Asn Val Ser Leu Asp Tyr Leu His Gly Arg Glu
        50                  55                  60

Ser Phe Glu Asp Thr Ser Leu Ser Lys Lys Gln Leu Thr Val Ala Ala
65                  70                  75                  80

His Ile Asp Asp Asp Val Ser Asp Thr Glu Met Asn Glu Ile Leu Ser
                85                  90                  95

Phe His
```

```
<210> SEQ ID NO 4
<211> LENGTH: 186
<212> TYPE: DNA
<213> ORGANISM: Artificial Sequence
<220> FEATURE:
<223> OTHER INFORMATION: Description of Artificial Sequence:
      Polynucleotide encoding IVI-3 polypeptide

<400> SEQUENCE: 4
atgagagatt ggctattgaa attgcgtata aaaataaaa tgactcaaga agaggttgcc      60
gttaaagcgg aaatttcaag aaccacatat gcatctattg aacagggaag aagaagaccg    120
tctgtggaaa gtgctatgcg aatcgcatca attttgggtt ttgattggac acttttttttt  180 gaataa                                                                186

<210> SEQ ID NO 5
<211> LENGTH: 61
<212> TYPE: PRT
<213> ORGANISM: Artificial Sequence
<220> FEATURE:
<223> OTHER INFORMATION: Description of Artificial Sequence:Deduced
      amino acid sequence for IVI-3 polypeptide

<400> SEQUENCE: 5

Met Arg Asp Trp Leu Leu Lys Leu Arg Ile Lys Asn Lys Met Thr Gln
  1               5                  10                  15

Glu Glu Val Ala Val Lys Ala Glu Ile Ser Arg Thr Thr Tyr Ala Ser
             20                  25                  30

Ile Glu Gln Gly Arg Arg Arg Pro Ser Val Glu Ser Ala Met Arg Ile
         35                  40                  45

Ala Ser Ile Leu Gly Phe Asp Trp Thr Leu Phe Phe Glu
     50                  55                  60

<210> SEQ ID NO 6
<211> LENGTH: 85
<212> TYPE: DNA
<213> ORGANISM: Artificial Sequence
<220> FEATURE:
<223> OTHER INFORMATION: Description of Artificial Sequence:
      Polynucleotide encoding a portion of an IVI-4 polypeptide

<400> SEQUENCE: 6
atgccagaaa aacaaaagat gattgatttc attttggaaa tcatgccaaa cgtaaagctt     60
attgttgaac tagcaacaga tgatc                                           85

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence:Deduced
      amino acid sequence of a portion of IVI-4 polypeptide

<400> SEQUENCE: 7

Met Pro Glu Lys Gln Lys Met Ile Asp Phe Ile Leu Glu Ile Met Pro
  1               5                  10                  15

Asn Val Lys Leu Ile Val Glu Leu Ala Thr Asp Asp
             20                  25

<210> SEQ ID NO 8
<211> LENGTH: 30
<212> TYPE: DNA
```

```
<213> ORGANISM: Artificial Sequence
<220> FEATURE:
<223> OTHER INFORMATION: Description of Artificial Sequence:PCR primer
      used in generating and expressing ivi-2 gene fragments

<400> SEQUENCE: 8
gtcgagtcga ctgatgttgc aaatgcactt                                           30

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:PCR primer
      used in generating and expressing ivi-2 gene fragments

<400> SEQUENCE: 9
gcagggtcga cgtcatcgtc tatatgagca                                           30

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:PCR primer
      used in generating and expressing ivi-2 gene fragments

<400> SEQUENCE: 10
catatgttcg gtacacgctt a                                                    21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:PCR primer
      used in generating and expressing ivi-2 gene fragments

<400> SEQUENCE: 11
atatgtcaat gaaaagagag                                                      20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:PCR primer
      used in expressing the ivi-3 gene product

<400> SEQUENCE: 12
catatggagg attggctatt g                                                    21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:PCR primer
      used in expressing the ivi-3 gene product

<400> SEQUENCE: 13
catatgttat tcaaaaaaaa g                                                    21
```